United States Patent
Zhu et al.

(10) Patent No.: US 11,174,239 B2
(45) Date of Patent: Nov. 16, 2021

(54) PEGYLATED THIOXANTHONE PHOTOINITIATOR AND PHOTOSENSITIVE RESIN COMPOSITION

(71) Applicants: JENKEM TECHNOLOGY CO., LTD. (BEIJING), Beijing (CN); JENKEM TECHNOLOGY CO., LTD. (TIANJIN), Tianjin (CN)

(72) Inventors: Hui Zhu, Beijing (CN); Meina Lin, Beijing (CN); Xuan Zhao, Beijing (CN)

(73) Assignees: JENKEM TECHNOLOGY CO., LTD. (BEIJING), Beijing (CN); JENKEM TECHNOLOGY CO., LTD. (TIANJIN), Tianjin (CN)

( * ) Notice: Subject to any disclaimer, the term of this patent is extended or adjusted under 35 U.S.C. 154(b) by 0 days.

(21) Appl. No.: 16/729,825

(22) Filed: Dec. 30, 2019

(65) Prior Publication Data
US 2020/0131147 A1 Apr. 30, 2020

Related U.S. Application Data

(63) Continuation of application No. PCT/CN2018/090825, filed on Jun. 12, 2018.

(30) Foreign Application Priority Data

Jun. 29, 2017 (CN) .......................... 201710518727.2
Jan. 16, 2018 (CN) .......................... 201810040940.1

(51) Int. Cl.
| | | |
|---|---|---|
| C08F 2/46 | (2006.01) | |
| C08F 2/50 | (2006.01) | |
| C08G 61/04 | (2006.01) | |
| C07D 335/16 | (2006.01) | |
| C08G 65/334 | (2006.01) | |
| C08K 5/18 | (2006.01) | |
| G03F 7/00 | (2006.01) | |
| G03F 7/031 | (2006.01) | |

(52) U.S. Cl.
CPC ....... *C07D 335/16* (2013.01); *C08G 65/3344* (2013.01); *C08K 5/18* (2013.01); *G03F 7/0037* (2013.01); *G03F 7/031* (2013.01)

(58) Field of Classification Search
CPC ............ C08G 65/3346; C08G 65/3344; C07D 335/16; C08K 5/18; G03F 7/0037; G03F 7/027; G03F 7/031
USPC .................. 522/7, 6, 184, 71, 1, 189; 520/1
See application file for complete search history.

(56) References Cited

U.S. PATENT DOCUMENTS

2013/0176370 A1* 7/2013 Loccufier ............ C09D 11/101
                                                                347/102
2017/0355864 A1* 12/2017 Zhou ........................ C08K 5/06

FOREIGN PATENT DOCUMENTS

| CA | 1243325 A | | 10/1988 | |
| CN | 1660837 | * | 8/2005 | |
| CN | 101090897 A | | 12/2007 | |
| CN | 104765251 A | | 7/2015 | |
| CN | 106633121 A | | 5/2017 | |
| CN | 106810627 | * | 6/2017 | |
| CN | 108084298 A | | 5/2018 | |
| JP | 2005068321 A | | 3/2005 | |
| WO | 9749664 A1 | | 12/1997 | |
| WO | 2008113390 A1 | | 9/2008 | |
| WO | WO-2016122736 A1 | * | 8/2016 | ............ C08G 65/48 |
| WO | 2016122455 A1 | | 4/2019 | |

OTHER PUBLICATIONS

Xie, CN 1660837 Machine Translation, Aug. 31, 2005 (Year: 2005).*
Dong et al., CN 106810627 Machine Translation, Jun. 9, 2017 (Year: 2017).*
The State Intellectual Property Office of People's Republic of China, First Office Action, Application No. 201810040940.1, dated Jun. 5, 2019.
The State Intellectual Property Office of People's Republic of China, The Second Office Action, Application No. 201810040940.1, dated Oct. 21, 2019.
The State Intellectual Property Office of People's Republic of China, The Third Office Action, Application No. 201810040940.1, dated May 29, 2020.
International Search Report, International application No. PCT/CN2018090825, Completion of international search Jul. 19, 2018, dated Aug. 6, 2018.
PCT Written Opinion of the International Searching Authority, International application No. PCT/CN2018/090825, International filing date Jun. 12, 2018, published Aug. 1, 2018.

* cited by examiner

*Primary Examiner* — Jessica Whiteley
(74) *Attorney, Agent, or Firm* — Flener IP & Business Law; Zareefa B. Flener

(57) ABSTRACT

The present invention discloses a PEGylated thioxanthone photoinitiator and a photosensitive resin composition, the PEGylated thioxanthone compound is eco-friendly and has low toxicity, high initiation efficiency and good thermal stability, meanwhile, as a kind of photoinitiator, the compound has a small amount of fragment residue after cured, and may improve the compatibility of the photoinitiator and photosensitive resin composition system. The photosensitive resin composition provided by the present invention has reasonable allocation of ingredients and content in the components thereof, capable of 3D-printing a hydrogel having a specific structure; the hydrogel has lower cytotoxicity and better biocompatibility, and may applied in bioengineering fields, e.g., 3D cell culture.

17 Claims, 3 Drawing Sheets

PEGYLATED THIOXANTHONE PHOTOINITIATOR AND PHOTOSENSITIVE RESIN COMPOSITION

CROSS-REFERENCE TO RELATED APPLICATION

This application is a continuation application of International patent application No. PCT/CN2018/090825, filed on Jun. 12, 2018, which claims priority to Chinese patent application No. CN201710518727.2, filed on Jun. 29, 2017, and Chinese patent application No. CN201810040940.1, filed on Jan. 16, 2018. All of the aforementioned patent applications are hereby incorporated by reference in their entireties.

TECHNICAL FIELD

The present invention relates to 3D printing technical field, and in particular to a PEGylated thioxanthone photoinitiator and a photosensitive resin composition containing the photoinitiator and an application thereof in 3D printing.

BACKGROUND 3D printing technology is a concept proposed relative to two-dimensional plane print, and Scans E. M. and Cima M. J., etc., of Massachusetts Institute of Technology applied for a patent on 3D printing (U.S. Pat. No. 5,204,055) in 1991 at the earliest. The 3D printing technique developed based upon the patent refers to a kind of powder molding by spraying bonding materials via a HP thermal-bubble nozzle. Similar to ink-jet printing, 3DP operating principle is a kind of rapid forming technique based upon drop injection principle, namely, stimulated by digital signal, liquid in the working chamber of nozzle forms liquid drops instantly and drops are sprayed to a specific position from the nozzle via certain rate and frequency, and finally, piled up layer by layer after cure to obtain forming parts. Thus, SLA (Sterolithography Apparatus), SLS (Selective Laser Sintered), FDM (Fused Deposition Modeling and other 3D printing techniques are developed.

Photocuring principle is relatively applied in 3D printing and is the most important 3D printing technical principle in early stage, and its implementation mode is as follows: a photosensitive liquid formula is utilized and cured into a certain shape under specific illumination, and then piled up layer by layer to obtain a final product. It is featured by rather high accuracy and rapid forming rate, and suitable for 3DP, SLA, DLP (Digital Light Procession) and other multiple 3D printing techniques.

In regard to the photosensitive 3D printing formula for photocuring principle, its main components are generally divided into: active component, photosensitizer, diluent and other components, wherein:

active component: active component refers to the component making liquid formula cured in a certain condition, and generally, it includes two or more active groups, capable of forming a network structure during reaction, thus forming the solid conforming to performance requirement. The active groups mainly include the following types: acrylic acids active groups, epoxy active groups, moreover, some other cationic monomers (e.g., oxa-butanes, spiro orthoester, bicyclic ortho ester, spiro ortho carbonate, cyclic lactones etc.);

photosensitizer: photosensitizer mainly refers to a photoinitiator, such kind of substance may produce free radicals, positive ions, etc., with the light illumination of specific wavelength, thus initiating the curing reaction of active substances. Moreover, the photosensitizer further includes light stabilizers, light inhibitors, light sensitizers and other components, used for regulating the curing reaction rate and degree of active substances;

diluent: diluent is divided into two types: one is inert diluent similar to solvent, and another one is active diluent containing the same active group as in the active component (only one active group generally), e.g.: monoacrylates, monoepoxy derivatives, etc; other components: it refers to the component for regulating formula performance or adding a certain performance of the formulas, including fillers, flatting agents, polymerization inhibitors, antisettling agents, dyes, pigments, etc.

Due to the particularity of 3D printing, a good photosensitive 3D printing formula needs to satisfy the following requirements:

1. Physical and chemical properties before curing: the liquid must be non-toxic, non-flammable, low volatile, free from dark reaction and sedimentation after being placed for a long time, meanwhile, the viscosity is low and pH≈7.

2. Curing performance: capable of being cured rapidly under specific light irradiation, low curing shrinkage rate. Additionally, the 3D printing material with special purpose should have stronger tensile strength, bending strength, hardness, toughness, chemical reagent resistance, zero deformation after being washed as well as good heat stability.

SUMMARY

One aspect of the present invention provides a PEGylated thioxanthone compound, including a structure shown in formula I,

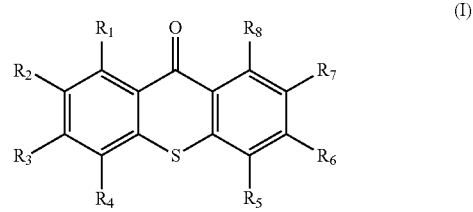

where, $R_{1-8}$ are independently selected from: H, OH, alkyl, alkoxy, aryl, aralkyl, aromatic or non-aromatic heterocyclyl, heterocycloalkyl, halogen and —X-PEG;

furthermore, at least one of $R_{1-8}$ is —X-PEG;

X is a linking group and selected from any one or a combination of two or more of the group consisting of: the above —$(CH_2)_i$—, —$(CH_2)_iO$—, —$(CH_2)_iS$—, —$(CH_2)_iCO$—, —$(CH_2)_iCOO$—, —$(CH_2)_iNH$—, —$(CH_2)_iCONH$—, —$(CH_2)_iOCOO$—, —$(CH_2)_iO$-CONH—, —$(CH_2)_iNHCONH$— and —$O(CH_2)_iCOO$—, wherein i is an integer of 0 to 10;

PEG is a polyethylene glycol and has the molecular weight of 200 Da-100 KDa.

Specifically, 1, 2, 3, 4, 5, 6, 7 or 8 of the $R_{1-8}$ may be —X-PEG; when 2 of the $R_{1-8}$ above are —X-PEGs, the —X-PEGs may be same or not exactly same.

Specifically, the alkyl is a $C_{1-6}$ alkyl, especially a $C_{1-3}$ alkyl, e.g., methyl, ethyl, n-propyl or isopropyl.

Specifically, the alkoxy is a $C_{1-6}$ alkoxy, especially a $C_{1-3}$ alkoxy, e.g., methoxyl, ethyoxyl, n-propoxy or isopropoxy.

Specifically, the halogen is F, Cl, Br or I, preferably F, Cl or Br, more preferably Cl.

Specifically, the aryl is selected from: phenyl, naphthyl, anthryl, phenanthryl, indenyl and pyrenyl.

Specifically, the heterocyclyl is a nitrogen-containing heterocyclic ring, such as five-membered rings or six-membered rings.

Specifically, the $R_{1-8}$ is independently selected from: H, OH, alkyl, alkoxy, halogen and —X-PEG, and at least one of $R_{1-8}$ is —X-PEG.

More specifically, the $R_{1-8}$ is independently selected from: H, methyl, methoxyl, F, Cl, Br, I and —X-PEG, and at least one of $R_{1-8}$ is —X-PEG.

In one embodiment of the present invention, the $R_2$ and/or $R_4$ are/is —X-PEG.

Specifically, the X is selected from any one or a combination of two or more of the group consisting of: —$(CH_2)_i$—, —$(CH_2)_iO$—, —$(CH_2)_iS$—, —$(CH_2)_iCO$—, —$(CH_2)_iNH$— and —$(CH_2)_iCONH$—; more specifically, the X is selected from: —$(CH_2)_i$—, —$(CH_2)_iO$— and —$(CH_2)_iCO$—.

In one embodiment of the present invention, the X is —$(CH_2)_i$—.

Specifically, the i is an integer of 0-5, e.g., 0, 1, 2, 3, 4 or 5.

Specifically, the X is selected from any one or a combination of two or more of the group consisting of: single bond, —$CH_2$—, —$CH_2CH_2$—, —$CH_2CH_2CH_2$—, —$CH_2CONHCH_2$—, —$CH_2CONHCH_2CH_2$—, —$CH_2CH_2CONHCH_2$—, —$CH_2CH_2CONHCH_2CH_2$—, —$CH_2NHCOCH_2$—, —$CH_2NHCOCH_2CH_2$—, —$CH_2CH_2NHCOCH_2$—, —$CH_2CH_2NHCOCH_2CH_2$—, —$OCH_2$—, —$OCH_2CH_2$, —$CH_2OCH_2$—, —$CH_2OCH_2CH_2$—, —$CH_2CH_2OCH_2$—, —$CH_2CH_2OCH_2CH_2$—, —$CH_2SCH_2$—, —$CH_2SCH_2CH_2$—, —$CH_2CH_2SCH_2$— and —$CH_2CH_2SCH_2CH_2$—.

In a further preferred embodiment of the present invention, the X is —$(CH_2)_i$—, and i=0, namely, X is a single bond.

The PEG is a linear, Y-shaped and multi-branched polyethylene glycol, including linear double-ended PEG, Y-shaped PEG, branched 4-armed PEG, branched 6-armed PEG or branched 8-armed PEG, etc.

In a particular embodiment, the PEG is a linear polyethylene glycol residue, having a structure shown in the general formula II:

$$CH_3O\text{---}(CH_2CH_2O)_{\overline{p}}\text{---} \quad (II)$$

where, p is an integer of 1-2000, preferably an integer of 10-1820, more preferably an integer of 10-230.

In a further particular embodiment, the PEG is a Y-shaped or U-shaped polyethylene glycol residue, having one of structures shown in the general formulas III or IV:

$$\begin{array}{c} CH_3O\text{---}(CH_2CH_2O)_{\overline{i}}\text{---}CH_2CH_2 \\ \phantom{CH_3O\text{---}(CH_2CH_2O)_{\overline{i}}\text{---}CH_2}\diagdown \\ \phantom{CH_3O\text{---}(CH_2CH_2O)_{\overline{i}}\text{---}CH_2}N\text{---} \\ \phantom{CH_3O\text{---}(CH_2CH_2O)_{\overline{i}}\text{---}CH_2}\diagup \\ CH_3O\text{---}(CH_2CH_2O)_{\overline{i}}\text{---}CH_2\text{---}C \\ \phantom{CH_3O\text{---}(CH_2CH_2O)_{\overline{i}}\text{---}CH_2\text{---}}\|\\ \phantom{CH_3O\text{---}(CH_2CH_2O)_{\overline{i}}\text{---}CH_2\text{---}}O \end{array} \quad (III)$$

$$\begin{array}{c} CH_3O\text{---}(CH_2CH_2O)_{\overline{n}}\text{---}\overset{O}{\overset{\|}{C}}\text{---}NHCH_2CH_2CH_2CH_2CH\text{---}\overset{O}{\overset{\|}{C}}\text{---} \\ \phantom{CH_3O\text{---}(CH_2CH_2O)_{\overline{n}}\text{---}C\text{---}NHCH_2CH_2CH_2CH_2CH}| \\ CH_3O\text{---}(CH_2CH_2O)_{\overline{n}}\text{---}\overset{\phantom{O}}{\underset{\|}{C}}\text{---}NH \\ \phantom{CH_3O\text{---}(CH_2CH_2O)_{\overline{n}}\text{---}C}O \end{array} \quad (IV)$$

where, n and i are integers of 1-1000, preferably integers of 5-910, more preferably integers of 5-120.

In a further particular embodiment, the PEG is a multi-branched polyethylene glycol residue, having a structure shown in the general formula V:

$$R\text{---}[(CH_2CH_2O)_{\overline{k}}]_j\text{---} \quad (V)$$

where, k is an integer of 1-600, preferably an integer of 3-80, more preferably an integer of 3-40.

j is an integer of 3-8,

R is a core molecule of the multi-branched polyethylene glycol, and R is selected from: a residue of pentaerythritol, oligomeric pentaerythritol, methyl glucoside, sucrose, diethylene glycol, propylene glycol, glycerol and polyglycerol; specifically, R is selected from: a residue of pentaerythritol, dipentaerythritol and tripolypentaerythritol.

In a preferred embodiment of the present invention, the PEG is a residue of linear polyethylene glycol, having a structure shown in general formula (II).

In a more preferred embodiment of the present invention, in the —X-PEG, X is a single bond, PEG is a residue of linear polyethylene glycol, having a structure shown in general formula (II), namely, the —X-PEG has the following structure:

$$CH_3O\text{---}(CH_2CH_2O)_{\overline{p}}\text{---}$$

where, p is an integer of 1-240, preferably, an integer of 1-120.

Specifically, the molecular weight of PEG may be 500-80000 Da (specifically, 500 Da, 1, 2, 3, 4, 5, 6, 7, 8, 9, 10, 15, 20, 25, 30, 35, 40, 45, 50, 55, 60, 65, 70, 75 or 80 KDa), etc.; more specifically, the molecular weight of PEG is 500-10000 Da, e.g., 500-5000 Da.

In one embodiment of the present invention, the molecular weight of PEG is 3500 Da.

In a preferred embodiment of the present invention, the PEGylated thioxanthone compound has a structure shown in the formula (VI):

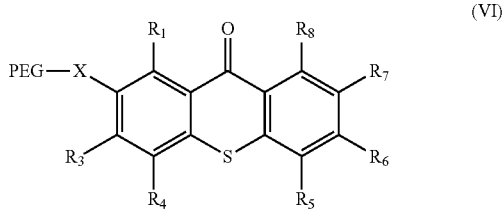

Where, the PEG, X, $R_1$ and $R_{2-8}$ are defined as the above present invention.

Specifically, in the formula (VI), the —X-PEG is

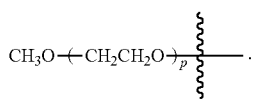

Specifically, in the formula (VI), the molecular weight of PEG is 500-80000 Da, preferably 500-10000 Da, more preferably 500-5000 Da.

Specifically, in the formula VI, the $R_1$ and $R_{2-8}$ are independently selected from: H, OH, alkyl, alkoxy, halogen; more specifically, the $R_1$ and $R_{2-8}$ are independently selected from: H, methyl, methoxyl, F, Cl, Br and I.

In a preferred embodiment of the present invention, the $R_1$ and $R_{5-8}$ are methyl, and meanwhile the PEGylated thioxanthone compound has a structure shown in the formula VII:

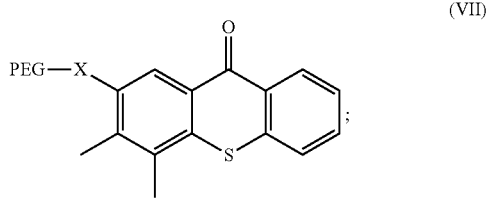

where, the PEG and X are defined as the above present invention.

Specifically, in the formula VII, the —X-PEG is

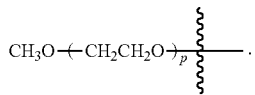

Specifically, in the formula VII, the molecular weight of PEG is 500-80000 Da, preferably 500-10000 Da, more preferably 500-5000 Da, specifically 3500 Da.

In a preferred embodiment of the present invention, the PEGylated thioxanthone compound has a structure shown in the formula VIII:

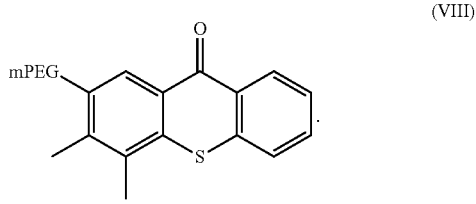

The mPEG is a residue of linear polyethylene glycol, having a structure shown in the general formula II, namely:

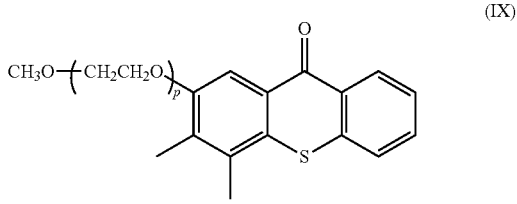

Specifically, molecular weight of the mPEG is 500-80000 Da, preferably 500-10000 Da, more preferably 500-5000 Da, specifically 3500 Da.

A further aspect of the present invention provides a photoinitiator, including the above PEGylated thioxanthone compound of the present invention.

A further aspect of the present invention provides a photosensitive resin composition, comprising a photosensitizer, wherein the photosensitizer includes the photoinitiator of the present invention.

Specifically, the composition further comprises an active component and a diluent.

Specifically, content (mass percent) of the components in the composition is respectively as follows: active component: 0.01-60%; diluent: 20-90%; photosensitizer: 0.01-20%.

Specifically, content (mass percent) of the active component in the composition is 1-40% (specifically 1%, 5%, 10%, 15%, 20%, 25%, 30%, 35% or 40%), preferably 10-30%.

Specifically, content (mass percent) of the diluent in the composition is 40-90% (specifically 40%, 45%, 50%, 55%, 60%, 65%, 70%, 75%, 80%, 85% or 90%), preferably 60-85%.

Specifically, content (mass percent) of the photoinitiator in the composition is 0.1-10.0% (specifically 0.1%, 0.5%, 1.0%, 1.5%, 2.0%, 2.5%, 3.0%, 4.0%, 5.0%, 6.0%, 7.0%, 8.0%, 9.0% or 10.0%), preferably 0.5-5.0%.

The active component of the present invention refers to PEG having one of the above active groups above, PEG-polyester copolymer or the like. The active group refers to the group capable of performing polymerization reaction, e.g., double bond, epoxy group, etc. Specifically, the active component includes but not limited to one or more of the following substances: PEG acrylate, PEG epoxy ether, monodispersed polyethylene glycol acrylate, monodispersed polyethylene glycol epoxy ether, diol diacrylate, diol dialkylene oxide, poly-substituted acrylic acids and small molecules such as epoxidized derivatives.

Specifically, in the active component, the PEG acrylate is PEG diacrylate or multi-armed PEG acrylate with 3-8 (specifically 3, 4, 5, 6, 7 or 8) arms.

Specifically, in the active component, the PEG epoxy ether is PEG diepoxy ether or multi-armed PEG epoxy ether with 3-8 (specifically 3, 4, 5, 6, 7 or 8) arms.

Specifically, in the active component, the molecular weight of PEG is 500 to 80000 Da (specifically 500, 1000, 5000, 10000, 20000, 30000, 40000, 50000, 60000, 70000 or 80000 Da), more preferably 1000-50000 Da; in one embodiment of the present invention, the molecular weight of PEG is 10000 Da.

Specifically, in the active component, the monodispersed polyethylene glycol acrylate is monodispersed polyethylene glycol diacrylate.

Specifically, in the active component, the monodispersed polyethylene glycol epoxy ether is monodispersed polyethylene glycol diepoxy ether.

Specifically, in the active component, the number of the condensated repeating units of the monodispersed polyethylene glycol is 2-50 (specifically 2, 5, 10, 15, 20, 25, 30, 35, 40, 45 or 50), preferably 2-40.

Specifically, in the active component, the diol is selected from: ethylene glycol, propylene glycol and butylene glycol.

In the active component, the acrylic acid and epoxy may be generally fully substituted, or partially substituted, and the number of substitution is more than 1.

In a preferred embodiment of the present invention, the active component is 8-armed polyethylene glycol acrylate (8arm-PEG-Aclt); in a more preferred embodiment of the present invention, molecular weight of the 8arm-PEG-Aclt is 10000 Da.

As for diacrylic acid derivatives and diepoxy derivatives of the monodispersed polyethylene glycols, the chemical formula thereof is the same as the corresponding PEG derivatives, and monodispersed polyethylene glycol is a compound (a single component with determined molecular weight) instead of a polymer, the number of the condensed glycols is 1-50, acrylic acid or epoxy is fully substituted.

The photosensitizer of the present invention is generally the substance capable of changing in a certain light condition. The most important component is photoinitiator, in addition, it is available to add proper amount of light stabilizer, light inhibitor and/or light sensitizer, etc., for regulating the reaction rate and time of the active components.

Specifically, the diluent includes inactive diluent and/or active diluent.

Specifically, the inactive diluent is a solvent, selected from: water, buffer solution, ethanol, isopropanol, DMSO, DMF, dioxane, THF and other water-soluble solvent with 70° C. boiling point above.

In one embodiment of the present invention, the diluent is water.

Specifically, the active diluent is the substance with an active group, including but not limited to one or more of the following substances: ethyl acrylate, butyl acrylate, isobutyl acrylate, epoxy propyl acrylate, ethyl methacrylate, butyl methacrylate, isobutyl methacrylate, epoxypropyl methacrylate, allyl methacrylate and other small-molecular free radical monomer as well as monomethoxyl PEG acrylate, monomethoxyl PEG epoxy ether, monomethoxyl monodispersed polyethylene glycol acrylate and monomethoxyl monodispersed polyethylene glycol epoxy ether.

Specifically, in the active diluent, the molecular weight of PEG is 500-80000 Da (specifically 500, 1000, 5000, 10000, 20000, 30000, 40000, 50000, 60000, 70000 or 80000 Da), more preferably 1000-50000 Da.

Specifically, in the active diluent, degree of glycol in the monodispersed polyethylene glycol is 2-50 (specifically 2, 5, 10, 15, 20, 25, 30, 35, 40, 45 or 50), more preferably 2-40.

Specifically, the photosensitive resin composition further includes auxiliary additive, the auxiliary additive is the inert substance not involving in photocuring, and generally the substance is added to satisfy some physico-chemical properties and special performance of the formed printing products; the auxiliary additive is selected from: one or more of co-initiator, antifoaming agent, flatting agent, polymerization inhibitor, antioxidant, antisettling agent, pigment, fluorescent agent, filler, wetting dispersant, flexibilizer, crosslinking agent, etc.

Specifically, content (mass percent) of the auxiliary additive in the composition is 0-10%, more preferably 0.01-10%.

A certain amount of antifoaming agent may be added to inhibit or eliminate bubbling in the photosensitive resin composition, thus achieving the advantages of low surface tension, strong defoaming capacity, good diffusivity and permeability as well as good gas permeability; specifically, the antifoaming agent is selected from: one or more of silicone antifoaming agents, mineral oil antifoaming agents, polyether antifoaming agents and fatty alcohol antifoaming agents.

A certain amount of flatting agent may be added to make materials achieving smooth and even surfaces; specifically, the flatting agent is selected from: one or more of acrylic acid flatting agents, silicone flatting agents and fluorocarbon flatting agents.

Specifically, the antioxidant is selected from: one or more of tetra(3, 5-ditertiary butyl-4-hydroxyl) pentaerithrityl phenylpropionate, tri(2, 4-ditertiary butyl) phenyl phosphite, N,N'-bis-(3-(3, 5-ditertiary butyl-4-hydroxyphenyl) propionyl) hexamethylenediamine, 2,6-ditertiary butyl-4-methylphenol and butylated hydroxyanisole.

A certain amount of polymerization inhibitor may be added to improve the storage stability of photosensitive resin composition, extend its service life and make it free from automatic curing within the term of validity; specifically, the polymerization inhibitor is selected from any one or a combination of two or more of the group consisting of: free radical inhibitors, phenolic inhibitors, inorganic compound inhibitors and metallo-organic compound inhibitors; in one embodiment of the present invention, the polymerization inhibitor is a phenolic inhibitor, e.g., hydroquinone.

Specifically, the co-initiator is selected from: one or more of triethanolamine, N,N-dimethyl benzylamine, N,N-dimethylaniline and triethylamine.

A certain amount of pigment may be added to make the photo-cured products having specific color; a certain amount of wetting dispersant may be added to improve the suspension stability of the pigment in the composition; those skilled in the art may choose the type and detailed component of the pigment.

In one embodiment of the present invention, the auxiliary additive includes a co-initiator, and content (mass percent) of the co-initiator in the photosensitive resin composition is 0.01-5.0% (specifically 0.01%, 0.1%, 0.5%, 1.0%, 1.5%, 2.0%, 3.0%, 4.0% or 5.0%), preferably 0.1-2.0%.

In a preferred embodiment of the present invention, the auxiliary additive includes an polymerization inhibitor, and content (mass percent) of the inhibitor in the photosensitive resin composition is 0-1%, preferably 0.001-1% (specifically 0.001%, 0.005%, 0.01%, 0.05%, 0.1%, 0.5% or 1%), preferably 0.001-0.1%, more preferably 0.005-0.05%.

In one embodiment of the present invention, the composition includes: active component, photoinitiator, diluent and co-initiator.

In another embodiment of the present invention, the composition includes: active component, photoinitiator, diluent, co-initiator and polymerization inhibitor.

In a preferred embodiment of the present invention, the composition includes: 8arm-PEG-Aclt, PEGylated thioxanthone compound shown in the formula IX of the present invention, triethanolamine and water.

In another preferred embodiment of the present invention, the photosensitive composition includes: 8-armed-PEG-Aclt, PEGylated thioxanthone compound shown in the formula IX of the present invention, triethanolamine, water and hydroquinone.

In a further preferred embodiment of the present invention, mass percent of components in the composition is respectively: 8-armed-PEG-Aclt: 10-30%, PEGylated thioxanthone compound shown in the formula IX of the present invention: 0.5-5.0%, triethanolamine: 0.1-2.0%, water: 60-85%, hydroquinone: 0.005-0.05%.

Specifically, the composition of the present invention further includes an auxiliary functional component so that the photosensitive composition possesses special functions.

Specifically, in the composition, content (mass percent) of the auxiliary functional component is 0-20.0%, preferably 0.1-20.0% (specifically 0.1%, 0.5%, 1.0%, 1.5%, 2.0%, 3.0%, 4.0%, 5.0%, 6.0%, 7.0%, 8.0%, 9.0%, 10.0%, 15.0% or 20.0%), more preferably 0.1-10.0%.

In one embodiment of the present invention, content (mass percent) of components of the composition is respectively: active component: 0.01-60%; diluent: 20-90%; photosensitizer: 0.01-20%, auxiliary functional component: 0-20%. The auxiliary functional component of the present invention includes but not limited to any one or a combination of two or more of the group consisting of: gelatin and acrylic acid-derived gelatin, hyaluronic acid and acrylic acid-derived hyaluronic acid, chitosan and modified chitosan, cellulose and carboxymethyl cellulose, alginate and modified alginate, collagen, agarose, various kinds of cell nutrient solution and other components capable of improving cell growth environment and regulating hydrogel mechanical property, and/or block polymer of multi-armed or linear polyethylene glycol polyester whose terminal group is modified by acrylate, which may make hydrogel possessing biodegradability. Specifically, in the above block polymer, the polyester chain portion is selected from any one or a combination of two or more of the group consisting of: polylactide, polyglycollide, glycolide-lactide copolymer, polycaprolactone, etc. More specifically, the polyester chain portion is a glycolide-lactide copolymer and/or polycaprolactone;

Specifically, in the block polymer, molecular weight of the polyester chain portion ranges from 800 to 80000 Da (specifically 800, 1000, 2000, 3000, 4000, 5000, 6000, 7000, 8000, 9000, 10000, 20000, 30000, 40000, 50000, 60000, 70000 or 80000 Da), more preferably 1000 to 40000 Da, further preferably 1000 to 10000 Da.

Specifically, in the block polymer of the multi-armed polyethylene glycol polyester, number of the arms is selected from an integer of 3-8 (specifically 3, 4, 5, 6, 7 or 8), more specifically, 4 or 8.

Specifically, in the block polymer, molecular weight of the multi-armed or linear PEG chain portion ranges from 800 to 80000 Da (specifically 800, 1000, 2000, 3000, 4000, 5000, 10000, 20000, 30000, 40000, 50000, 60000, 70000 or 80000 Da), more preferably 2000 to 40000 Da.

In one embodiment of the present invention, and in the composition, the auxiliary functional component is selected from any one or a combination of two or more of the group consisting of: gelatin and acrylic acid-derived gelatin, hyaluronic acid and acrylic acid-derived hyaluronic acid, chitosan and modified chitosan, cellulose and carboxymethyl cellulose, alginate and modified alginate, collagen, agarose, cell nutrient solution and other components capable of improving cell growth environment and regulating hydrogel mechanical property; specifically, content (mass percent) of the auxiliary functional component in the composition is 0.1-10.0%, preferably 0.5-5.0%.

In one embodiment of the present invention, and in the composition, the auxiliary functional component is acrylic acid-derived hyaluronic acid (HA-Aclt).

In another preferred embodiment of the present invention, and in the composition, the auxiliary functional component is acrylic acid-derived gelatin (Gel-Aclt).

In another embodiment of the present invention, and in the composition, the auxiliary functional component is a block polymer of multi-armed or linear PEG polyester whose terminal group is modified by acrylate; specifically, content of the auxiliary functional component in the composition is 0.1-20.0%, more preferably 1-10%.

In a preferred embodiment of the present invention, and in the composition, the auxiliary functional component is a block polymer of multi-armed PEG polycaprolactone whose terminal group is modified by acrylate, where, molecular weight of the polycaprolactone chain ranges from 800 to 80000 Da, preferably 1000 to 40000 Da, further preferably 1000 to 10000 Da; further preferably 1000 to 10000 Da; the molecular weight of PEG chain portion ranges from 800 to 80000 Da, preferably 2000 to 40000 Da; number of the arms is selected from an integer of 3-8, preferably 4 or 8.

In a further preferred embodiment of the present invention, and in the composition, the auxiliary functional component is a block polymer of 8-armed PEG polycaprolactone whose terminal group is modified by acrylate: 8arm-PEG10k-PCL3k-Aclt (where molecular weight of the polycaprolactone chain is 3000 Da, and the molecular weight of PEG chain portion is 10000 Da).

A further aspect of the present invention provides an application of the above PEGylated thioxanthone compound and photosensitive resin composition in the preparation of 3D printing consumables.

Specifically, in the above application, the 3D printing includes 3DP, SLA, DLP and other 3D printing modes.

A further aspect of the present invention provides a hydrogel obtained by 3D printing the above photosensitive resin composition.

A further aspect of the present invention provides an application of the above hydrogel in cell culture.

The PEGylated thioxanthone compound provided by the present invention is eco-friendly and has low toxicity, high initiation efficiency and good thermal stability, meanwhile, as a kind of photoinitiator, the compound has a small amount of fragment residue after being cured, and may improve the compatibility of the photoinitiator and photosensitive resin composition system. The photosensitive resin composition provided by the present invention has reasonable allocation of ingredients and content in the components thereof, capable of 3D-printing a hydrogel having a specific structure; the hydrogel has lower cytotoxicity and better biocompatibility, and may be applied in bioengineering fields.

DETAILED DESCRIPTION OF THE EMBODIMENTS

Unless otherwise defined, all technical and scientific terms used herein have the same meaning as commonly understood by those skilled in the art in which the present invention involves, e.g.:

"alkyl" refers to linear or branched hydrocarbon-chain free radical without unsaturated bond, $C_{1-6}$ alkyl refers to a linear or branched alkyl containing 1-6 carbon atoms, e.g., methyl, ethyl, n-propyl, isopropyl, n-butyl, isobutyl, tertiary butyl, n-amyl, n-hexyl, etc.; if alkyl is substituted by aryl, it is an "aralkyl" free radical accordingly, $C_{7-14}$ aralkyl refers to an aralkyl containing 7-14 carbon atoms, e.g., benzyl, benzhydryl or phenethyl, etc.; if alkyl is substituted by heterocyclyl, it is a "heterocyclyl alkyl" accordingly.

"alkoxy" refers to a substituent group formed by that H in hydroxyl thereof is substituted by alkyl, $C_{1-6}$ alkoxy refers to an alkoxy containing 1-6 carbon atoms, e.g., methoxyl, ethyoxyl, propoxy, butoxy, etc.

"aryl" refers to a monocyclic or polycyclic free radical, including a polycyclic free radical with mono-aryl group and/or fused aryl group, e.g., the one containing 1-3 simple or fused ring(s) and 6-18 carbocyclic atoms, e.g., phenyl, xenyl, naphthyl, anthryl, phenanthryl, indenyl, pyrenyl, etc. "heterocyclyl" includes a heteroaromatic group and heteroalicyclic group containing 1-3 monocyclic or fused rings as well as 3 to about 18 carbocyclic atoms. Proper heteroaryl in the compound of the present invention contains 1, 2 or 3 kinds of heteroatom, and the heteroatom is selected from atom N, O or S, preferably N.

In the present invention, as for the definition of the linking group X, the "combination" refers to a group formed by bonding two or more of the linking groups via a chemical bond, for example, combination of $-(CH_2)_i-$ and $-(CH_2)_iCONH-$ may be $-(CH_2)_iCONH(CH_2)_j-$, specifically, combination of $-CH_2-$ and $-CH_2CH_2CONH-$ may be $-CH_2CH_2CONHCH_2-$, $-CH_2CH_2CONH-$. The "combination" serves to define the chemical structure of the linking group instead of preparation steps and combining sequence of the linking group, etc.

The polyethylene glycol in the present invention is preferably characterized by molecular weight, and secondly by the number of repeating units.

The technical solution of the present invention will be described clearly and completely hereafter with reference to embodiments of the present invention, apparently, embodiments described herein are only a part of embodiments of the present invention, and are not all of embodiments thereof. Based on the embodiments of the present invention, all other embodiments obtained by those skilled in the art without any creative efforts are within the protection scope of the present invention.

Figure 1:
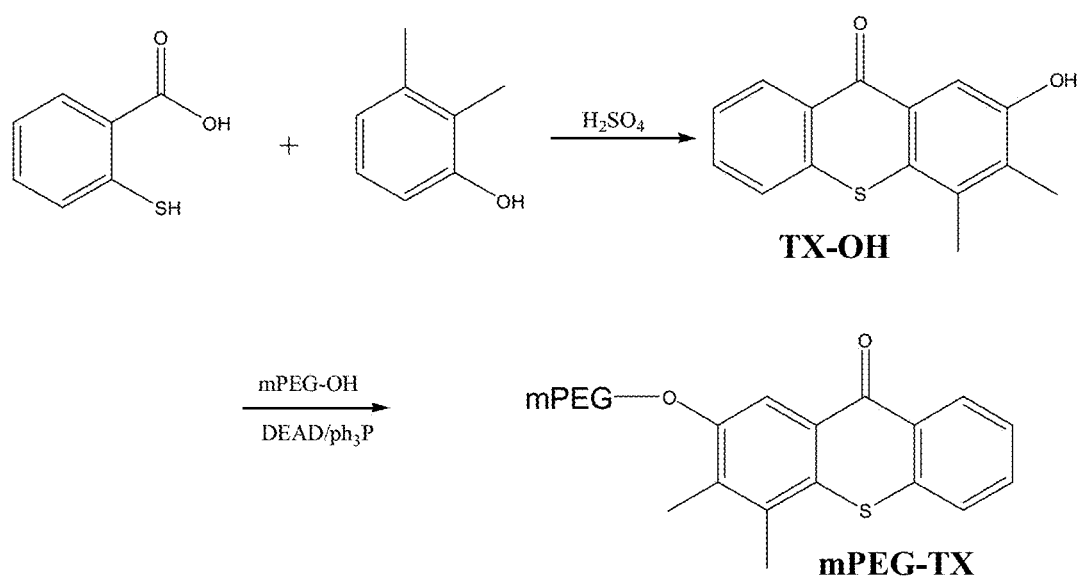
FIG. 1 shows a synthetic route diagram of mPEG-TX provided by Embodiment 1.

Embodiment 1: mPEG-TX Synthesis mPEG-TX synthetic route is shown in FIG. 1, and specific steps are as follows:

Thiosalicylic acid (6 g, 38.9 mmol) were added to concentrated sulfuric acid (45 mL) and stirred for 5 min for mixing evenly (ice-water bath). 2,3-dimethylphenol (14.25 g, 116 mmol) were added to the mixed solution during stirring in batches within 30 min, the mixed solution was stirred for 2 h at 10° C., and heated up to the temperature of high-temperature reaction, then stirred for 3 h, and at the end of reaction, the reaction liquid was placed at room temperature over night. In stirring condition, reaction liquid was put into 10 times (volume) of boiling water for boiling for 5 min, and filtered after cooling, the filtrate was recrystallized by water and dioxane (20:80, V/V). Finally, about 7.8 g intermediate TX-OH was obtained. NMR: 7.5-8.4 5H, H on benzene ring; 2.51, 3H, methyl H; 2.25, 3H, methyl H.

mPEG (14 g, 4 mmol, molecular weight: 3500 Da) and methylbenzene were co-boiled for water removal and cooling, then added TX-OH (2.56 g, 10 mmol) and ph3P (2620 mg, 10 mmol), DIAD (diisopropyl azodiformate) (1.4 mL, 8 mmol) were added dropwise for reaction at room temperature over night, and the solution was filtered and concentrated to obtain isopropanol/ether precipitate, where the solution turned red slowly with the addition of DIAD and the reaction was monitored by HPLC, finally, ether was fully washed to remove DIAD and dried to obtain 12.5 g product. HPLC(>95%), NMR: 7.4-8.5 5H, H on benzene ring; 3.4-0.38:320H, H on mPEG; 3.3, 3H, CH3O; 2.55, 3H, methyl H; 2.23, 3H, methyl H.

Figure 2:
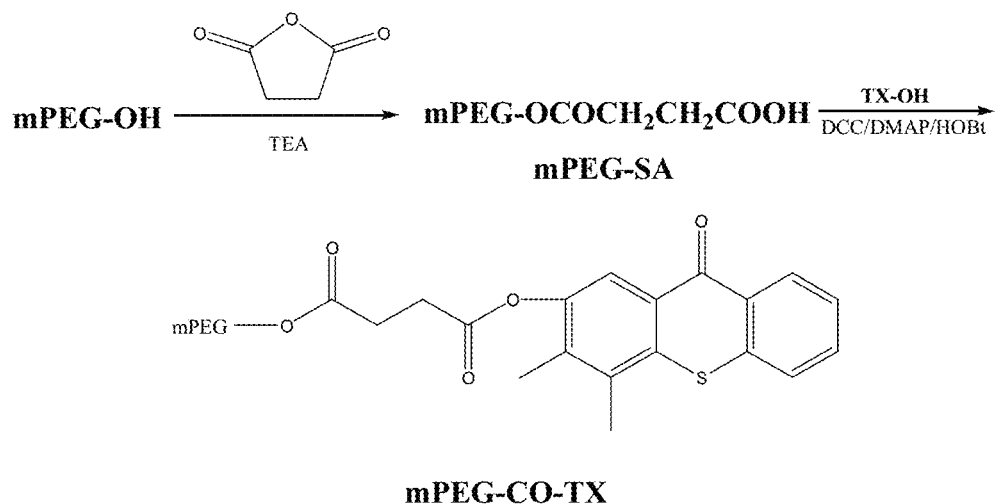
FIG. 2 shows a synthetic route diagram of mPEG-CO-TX provided by Embodiment 2.

Embodiment 2: mPEG-CO-TX Synthesis mPEG-CO-TX synthetic route is shown in FIG. 2, and specific steps are as follows:

mPEG (14 g, 4 mmol, molecular weight: 3500 Da) were added to succinic anhydride (0.5 g, 5 mmol, 100), slightly heated (about 37° C.), dissolved by stirring, then added TEA (0.83 mL, 6 mmol) for reacting over night, it was detected by HPLC and washed for once. The solution was concentrated to obtain isopropanol precipitate, and ether was washed to obtain 13 g intermidate mPEG-SA. HPLC>97%, NMR: 4.1, 2H, CH2OCO; 3.4-3.8, 310H, H on PEG; 3.3, 3H, CH3O; 2.3-2.5, 2-group H, 2 for each group, OCOCH2CH2COOH.

DCC (165 mg, 0.8 mmol), DMAP (12 mg, 0.1 mmol), QTX-1(203 mg, 0.8 mmol), HOBt (108 mg, 0.8 mmol) and DCM (30 mL) were added to mPEG-SA (2.35 g, 0.67 mmol) for stirring over night at room temperature, and by HPLC monitoring, the reaction was almost complete. The solution was concentrated to obtain precipitate, and the precipitate was filtered to obtained 2.3 g product. HPLC(>95%), NMR: 7.4-8.5 5H, H on benzene ring; 4.3, 2H, CH2OCO; 3.4-3.8, 310H, H on PEG; 3.3, 3H, CH3O; 2.8-3.0, 2-group H, 2 for each group, OCOCH2CH2COOH; 2.55, 3H, methyl H; 2.23, 3H, methyl H.

Embodiment 3: Contrast of the Two Photoinitiators mPEG-TX and mPEG-CO-TX

Preparation of Solution A and B:

Solution A: 8arm-PEG-Aclt (500 mg), mPEG-TX (17 mg, prepared by Embodiment 1) were added to water (1.5 mL), and then triethanolamine (40 µL) were added.

Solution B: 8arm-PEG-Aclt (500 mg), mPEG-CO-TX (17 mg, prepared by Embodiment 2) were added to water (1.5 mL), and then triethanolamine (40 µL) were added.

Figure 3:
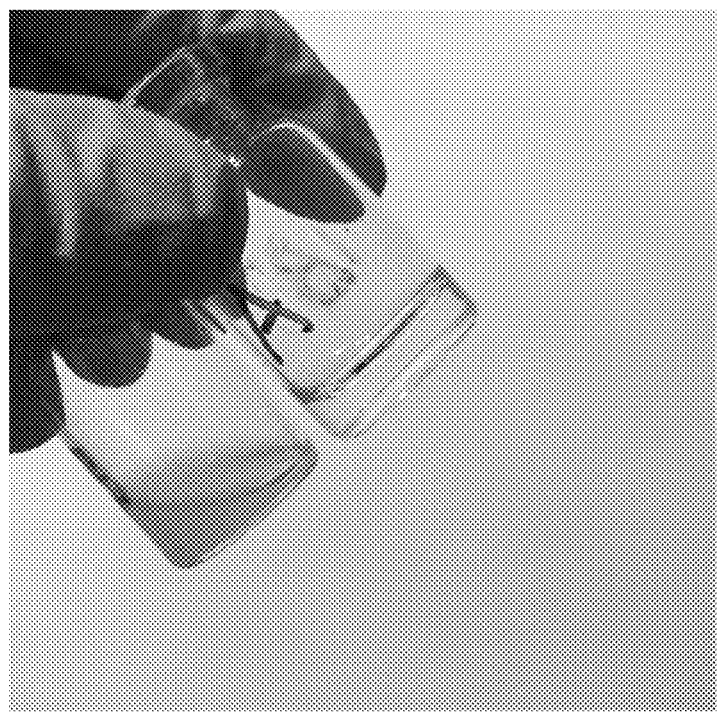
FIG. 3 shows the initiating effect of mPEG-TX and mPEG-CO-TX provided by Embodiment 3 as a photoinitiator respectively, the left denotes solution B and the right denotes solution A.

Standing for 12 h, solution A and B were put into a constant-temperature illumination box (22° C., 2750 Lux) after defoaming, and then taken out after being illuminated for 60 min, as shown in FIG. 3, transparent yellow hydrogel formed in bottle A (containing mPEG-TX), but no hydrogel formed in bottle B and the liquid turned opaque because ester bond was hydrolyzed into water-insoluble TX-OH. It can be seen from the experiment that compared with mPEG-CO-TX formed by linking molecules PEG and TX via ester bond, mPEG-TX prepared by Embodiment 1 had better photoinitiating effect and higher stability.

Embodiment 4: Formula 1 and 3D Printing Thereof

TABLE 1

Component and content of the formula 1

| Component | Content |
| --- | --- |
| 8arm-PEG$_{10k}$-Aclt | 25% |
| Photoinitiator (mPEG$_{3500}$-TX) | 1% |
| Triethanolamine | 0.9% |
| Water | 73.09% |
| Hydroquinone | 0.01% |
| Total quantity | 100% |

100 g solution was prepared according to the formula of table 1. 100 g solution was put into a resin tank of a BESK 3D printer (1510) for 3D printing by Q3DP software. The obtained product was solid yellow hydrogel.

Embodiment 5: Formula 2 and 3D Printing Thereof

TABLE 2

Component and content of the formula 2

| Component | Content |
| --- | --- |
| 8arm-PEG$_{10k}$-Aclt | 20% |
| Photoinitiator (mPEG$_{3500}$-TX) | 1% |
| Water | 78.09% |
| Triethanolamine | 0.9% |
| Hydroquinone | 0.01% |
| Total quantity | 100% |

100 g solution was prepared according to the formula of table 2. 100 g solution was put into a resin tank of a BESK 3D printer (1510) for 3D printing by Q3DP software. The obtained product was solid yellow hydrogel.

Embodiment 6: Formula 3 and 3D Printing Thereof

TABLE 3

Component and content of the formula 3

| Component | Content |
| --- | --- |
| 8arm-PEG$_{10k}$-Aclt | 15% |
| Photoinitiator (mPEG$_{3500}$-TX) | 1% |
| Water | 83.09% |
| Triethanolamine | 0.9% |
| Hydroquinone | 0.01% |
| Total quantity | 100% |

100 g solution was prepared according to the formula of table 3. 100 g solution was put into a resin tank of a BESK 3D printer (1510) for 3D printing by Q3DP software. The obtained product was solid yellow hydrogel.

Embodiment 7: Formula 4 and 3D Printing Thereof

TABLE 4

Component and content of the formula 4

| Component | Content |
| --- | --- |
| 8arm-PEG$_{10k}$-Aclt | 30% |
| Photoinitiator (mPEG$_{3500}$-TX) | 1% |
| Water | 68.09% |
| Triethanolamine | 0.9% |
| Hydroquinone | 0.01% |
| Total quantity | 100% |

100 g solution was prepared according to the formula of table 4. 100 g solution was put into a resin tank of a BESK 3D printer (1510) for 3D printing by Q3DP software. The obtained product was solid yellow hydrogel.

Embodiment 8: Formula 5 and 3D Printing Thereof

| Component | Content |
| --- | --- |
| 8arm-PEG$_{10k}$-Aclt | 25% |
| Photoinitiator (mPEG$_{3500}$-TX) | 1.7% |
| Water | 72.79% |
| Triethanolamine | 0.5% |
| Hydroquinone | 0.01% |
| Total Quantity | 100% |

100 g solution was prepared according to the formula of table 5. 100 g solution was put into a resin tank of a BESK 3D printer (1510) for 3D printing by Q3DP software. The obtained product was solid yellow hydrogel.

Embodiment 9: Formula 6 and 3D Printing Thereof

TABLE 6

Component and content of the formula 6

| Component | Content |
| --- | --- |
| 8arm-PEG$_{10k}$-Aclt | 25% |
| Photoinitiator (mPEG$_{3500}$-TX) | 3.4% |

TABLE 6-continued

Component and content of the formula 6

| Component | Content |
|---|---|
| Water | 0.9% |
| Triethanolamine | 70.69% |
| Hydroquinone | 0.01% |
| Total quantity | 100% |

100 g solution was prepared according to the formula of table 6. 100 g solution was put into a resin tank of a BESK 3D printer (1510) for 3D printing by Q3DP software. The obtained product was solid yellow hydrogel.

Embodiment 10: Formula 7 and 3D Printing Thereof

TABLE 7

Component and content of the formula 7

| Component | Content |
|---|---|
| 8arm-$PEG_{10k}$-Aclt | 25% |
| Photoinitiator (m$PEG_{3500}$-TX) | 7.1% |
| Triethanolamine | 1.9% |
| Water | 65.99% |
| Hydroquinone | 0.01% |
| Total quantity | 100% |

100 g solution was prepared according to the formula of table 7. 100 g solution was put into a resin tank of a BESK 3D printer (1510) for 3D printing by Q3DP software. The obtained product was solid yellow hydrogel.

Embodiment 11: Formula 8 and 3D Printing Thereof

TABLE 8

Component and content of the formula 8

| Component | Content |
|---|---|
| 8arm-$PEG_{10k}$-Aclt | 25% |
| Photoinitiator (m$PEG_{3500}$-TX) | 1.7% |
| Triethanolamine | 0.2% |
| Water | 73.09% |
| Hydroquinone | 0.01% |
| Total quantity | 100% |

100 g solution was prepared according to the formula of table 8. 100 g solution was put into a resin tank of a BESK 3D printer (1510) for 3D printing by Q3DP software. The obtained product was solid yellow hydrogel.

Embodiment 12: Formula 9 and 3D Printing Thereof

TABLE 9

Component and content of the formula 9

| Component | Content |
|---|---|
| 8arm-$PEG_{10k}$-Aclt | 20% |
| Photoinitiator (m$PEG_{3500}$-TX) | 1.7% |
| Triethanolamine | 0.2% |
| Water | 78.09% |
| Hydroquinone | 0.01% |
| Total quantity | 100% |

100 g solution was prepared according to the formula of table 9. 100 g solution was put into a resin tank of a Form2 3D printer from FormLab company for 3D printing. The obtained product was solid yellow hydrogel.

Embodiment 13: Formula 10 and 3D Printing Thereof

TABLE 10

Component and content of the formula 10

| Component | Content |
|---|---|
| 8arm-$PEG_{10k}$-Aclt | 25% |
| Gel-Aclt | 1% |
| Photoinitiator (m$PEG_{3500}$-TX) | 1.7% |
| Triethanolamine | 0.2% |
| Water | 72.1% |
| Total quantity | 100% |

Note: Gel-Aclt is acrylic acid-derived gelatin.

100 g solution was prepared according to the formula of table 10. 100 g solution was put into a resin tank of a Form2 3D printer from FormLab company for 3D printing. The obtained product was solid yellow hydrogel.

Embodiment 14: Formula 11 and 3D Printing Thereof

TABLE 11

Component and content of the formula 11

| Component | Content |
|---|---|
| 8arm-$PEG_{10k}$-Aclt | 25% |
| HA-Aclt | 2% |
| Photoinitiator (m$PEG_{3500}$-TX) | 1.7% |
| Triethanolamine | 0.2% |
| Water | 71.09% |
| Hydroquinone | 0.01% |
| Total quantity | 100% |

Note: HA-Aclt is acrylic acid-derived hyaluronic acid.

100 g solution was prepared according to the formula of table 11. 100 g solution was put into a resin tank of a Form2 3D printer from FormLab company for 3D printing. The obtained product was solid yellow hydrogel.

Embodiment 15: Formula 12 and 3D Printing Thereof

TABLE 12

Component and content of the formula 12

| Component | Content |
| --- | --- |
| 8arm-PEG$_{10k}$-Aclt | 25% |
| Photoinitiator (mPEG$_{3500}$-TX) | 1.7% |
| Triethanolamine | 0.2% |
| Water | 73.1% |
| Total quantity | 100% |

Figure 4:
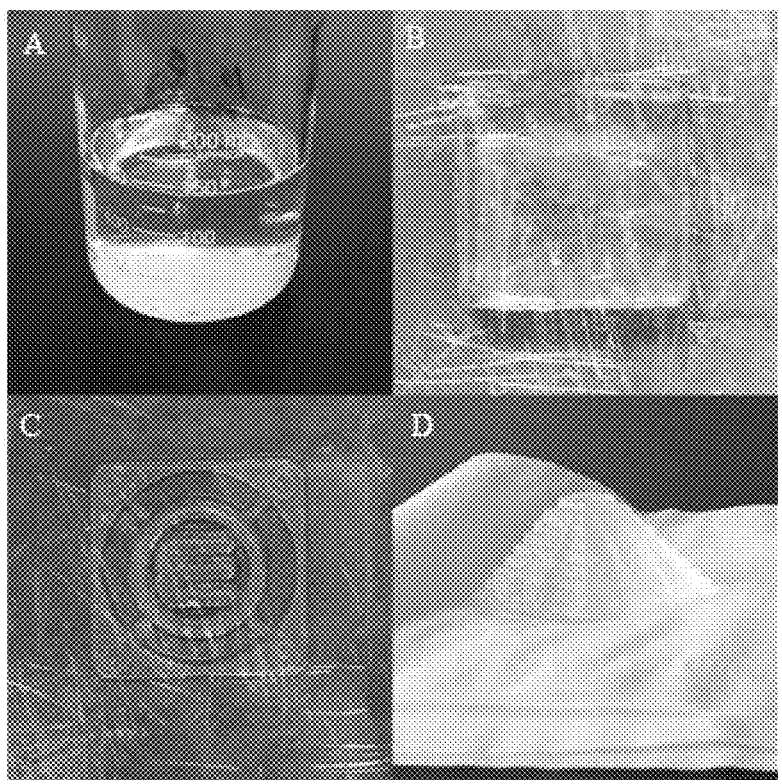
FIG. 4 shows a formula-based solution provided by Embodiment 15 and solid hydrogel obtained by 3D printing, wherein, figure A denotes the solution prepared based upon the formula of Embodiment 15, figures B, C, D respectively denote different shapes and structures of solid hydrogel prepared by 3D printing the above formula-based solution.

150 g solution was prepared according to the formula of table 12, as shown in figure A of FIG. 4. 150 g solution was put into a resin tank of a Form2 3D printer from FormLab company for 3D printing. The obtained product was solid faint yellow-yellow hydrogel, as shown in figures B, C and D of FIG. 4.

Solution of the above formula has moderate viscosity and fluidity, rapid forming speed of gel as well as mild conditions, moreover, it is easy to print and mold, and free from blocking the nozzle. The gel obtained by 3D printing has good molding property, small volume shrinkage, good strength, moderate hardness and good biocompatibility, meanwhile, the gel may maintain its shape and structure, free from collapse and swelling.

Embodiment 16: Formula 13 and 3D Printing Thereof

TABLE 13

Component and content of the formula 13

| Component | Content |
| --- | --- |
| 8arm-PEG$_{10k}$-Aclt | 25% |
| 8arm-PEG$_{10k}$-PCL$_{3k}$-Aclt | 1.3% |
| Photoinitiator (mPEG$_{3500}$-TX) | 1.7% |
| Triethanolamine | 0.2% |
| Water | 71.8% |
| Total quantity | 100% |

Note: in the table, 8arm-PEG10k-PCL3k-Aclt is a block polymer of 8-armed PEG polyester modified by acrylate, of which, the polyester chain portion is polycaprolactone, and molecular weight of the PEG chain portion is 10 KDa, molecular weight of the polyester chain portion is 3 KDa.

Figure 5:
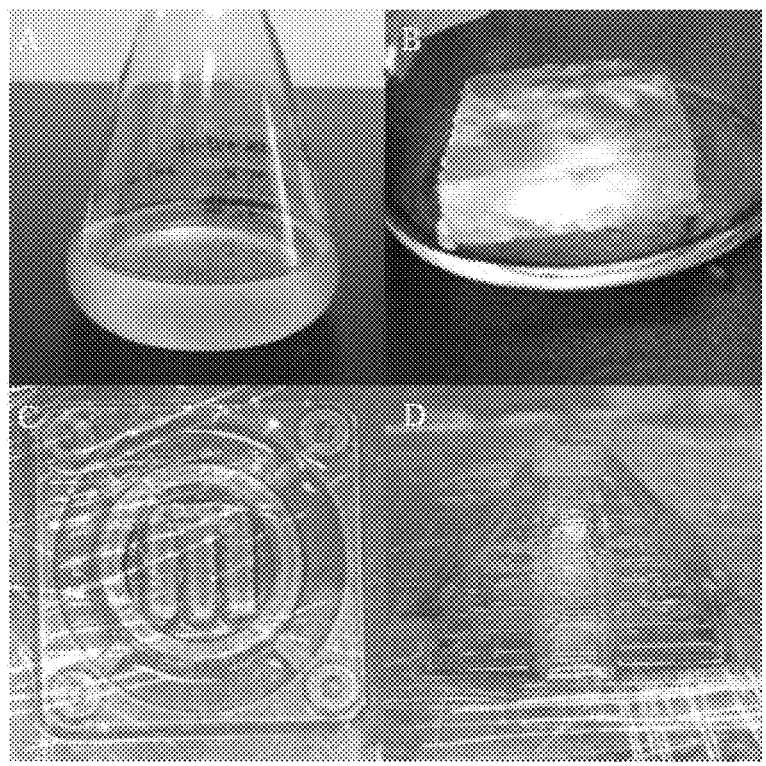
FIG. 5 shows a formula-based solution provided by Embodiment 16 and solid hydrogel obtained by its 3D printing, where, figure A denotes the solution prepared based upon the formula of Embodiment 16, figures B, C, D respectively denote different shapes and structures of solid hydrogel prepared by 3D printing the above formula-based solution.

150 g solution was prepared according to the formula of table 13, as shown in figure A of FIG. 5. 150 g solution was put into a resin tank of a Form2 3D printer from FormLab company for 3D printing. The obtained product was solid faint yellow-yellow hydrogel, as shown in figures B, C and D of FIG. 5.

Solution of the above formula has moderate viscosity and fluidity, rapid forming speed of gel as well as mild conditions, moreover, it is easy to print and mold, and free from blocking the nozzle. The gel obtained by 3D printing has good molding property, small volume shrinkage, good strength, moderate hardness and good biocompatibility, meanwhile, the gel may maintain its shape and structure, free from collapse and swelling.

In the formula of Embodiments 4-16 of the present invention, the content refers to mass percent, all photoinitiators used (mPEG3500-TX) are all products prepared by Embodiment 1, and the 8arm-PEG10k-Aclt used is provided by JenKem, has the molecular weight of 10 KDa and the following structure:

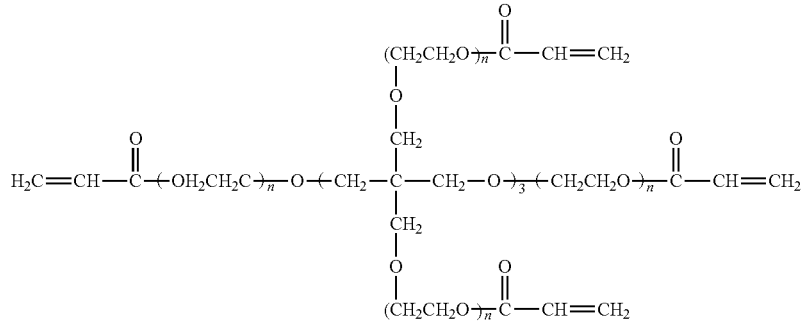

What is described above are merely preferred embodiments of the present invention, and are not to limit the present invention; any modification and equivalent replacement, etc. within the spirit and principle of the present invention shall be covered in the protection scope of the present invention.

What is claimed is:

1. A PEGylated thioxanthone compound, comprising a structure shown in the formula VII,

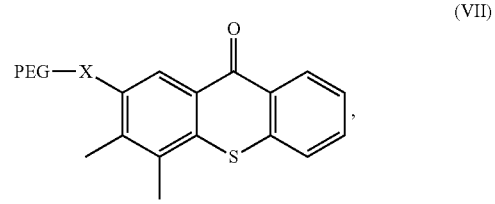
(VII)

X is a linking group and selected from any one or a combination of two or more of the group consisting of: the above —(CH$_2$)$_i$O—, —(CH$_2$)$_i$S—, —(CH$_2$)$_i$NH—, —(CH$_2$)$_i$CONH—, and —(CH$_2$)$_i$NHCONH—, wherein i is an integer of 0 to 10;

PEG is a polyethylene glycol residue and has the molecular weight of 2000 Da-10000 Da.

2. The compound according to claim 1, wherein i is an integer of 0 to 5.

3. The compound according to claim 1, wherein the PEG is a linear polyethylene glycol residue and has a structure shown in the general formula II:

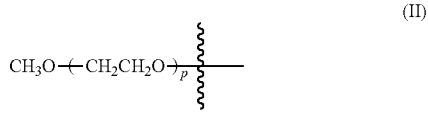

wherein, p is an integer of 45 to 226;
or,
the PEG is a Y-shaped or U-shaped polyethylene glycol residue and has one of structures shown in general formulas III or IV:

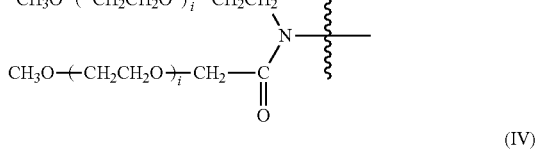

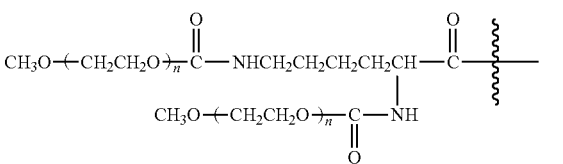

wherein, n and i are independently selected from an integer of 23 to 113.

4. The compound according to claim 3, wherein the PEG is a linear polyethylene glycol residue and has a structure shown in the general formula II.

5. The compound according to claim 1, wherein the molecular weight of PEG ranges from 3000 Da to 5000 Da.

6. A photoinitiator, comprising the PEGylated thioxanthone compound according to claim 1.

7. A photosensitive resin composition, comprising a photosensitizer, wherein the photosensitizer comprises the photoinitiator according to claim 6;
preferably, the composition further comprises an active component (such as 8-armed polyethylene glycol acrylate) and a diluent;
more preferably, content of the active component in the composition ranges from 1% to 40%, preferably 10% to 30%; and/or,
content of the diluent in the composition ranges from 40% to 90%, preferably 60% to 85%; and/or,
content of the photoinitiator in the composition ranges from 0.1%, preferably 0.5% to 5%.

8. The photosensitive resin composition according to claim 7, wherein the active component is selected from: one or more of PEG acrylate, PEG epoxy ether, monodispersed polyethylene glycol acrylate, monodispersed polyethylene glycol epoxy ether, diol diacrylate and diol dialkylene oxide.

9. The photosensitive resin composition according to claim 8, wherein the PEG acrylate is PEG diacrylate or PEG acrylate with 3-8 arms; and/or,
the PEG epoxy ether is PEG diepoxy ether or PEG epoxy ether with 3-8 arms; and/or,
the monodispersed polyethylene glycol acrylate is monodispersed polyethylene glycol diacrylate; and/or,
the monodispersed polyethylene glycol epoxy ether is monodispersed polyethylene glycol diepoxy ether; and/or,
the diol is selected from: ethylene glycol, propylene glycol and butylene glycol.

10. The photosensitive resin composition according to claim 7, wherein the diluent comprises an inactive diluent and/or an active diluent;
preferably, the inactive diluent is solvent, and selected from: water, buffer solution, ethanol, isopropanol, DMSO, DMF, dioxane and THF; and/or,
the active diluent is selected from: one or more of ethyl acrylate, butyl acrylate, isobutyl acrylate, epoxy propyl acrylate, ethyl methacrylate, butyl methacrylate, isobutyl methacrylate, epoxypropyl methacrylate, allyl methacrylate, monomethoxyl PEG acrylate, monomethoxyl PEG epoxy ether, monomethoxyl monodispersed polyethylene glycol acrylate and monomethoxyl monodispersed polyethylene glycol epoxy ether.

11. The photosensitive resin composition according to claim 8, wherein the molecular weight of PEG ranges from 500 Da to 80000 Da; and/or, polymerization degree of the ethylene glycol in the monodispersed polyethylene glycol is 2-50.

12. The photosensitive resin composition according to claim 7, wherein the photosensitive resin composition further comprises an auxiliary additive;
the auxiliary additive is selected from: one or more of co-initiator, antifoaming agent, flatting agent, polymerization inhibitor, antioxidant, antisettling agent, pigment, fluorescent agent, filler, wetting dispersant, flexibilizer and cross-linking agent;
content of the auxiliary additive in the composition ranges from 0% to 10%;
preferably,
the auxiliary additive comprises a co-initiator;
the co-initiator is selected from: one or more of triethanolamine, N,N-dimethyl benzylamine, N,N-dimethylaniline and triethylamine;
content of the co-initiator in the photosensitive resin composition ranges from 0% to 5%;
and/or,
the auxiliary additive comprises a polymerization inhibitor;
the polymerization inhibitor is selected from: one or more of phenolic polymerization inhibitors, quinone polymerization inhibitors, aromatic nitro-compound polymerization inhibitors and inorganic compound polymerization inhibitors;
content of the polymerization inhibitor in the photosensitive resin composition ranges from 0% to 1%.

13. The photosensitive resin composition according to claim 7, wherein the composition further comprises an auxiliary functional component;
preferably, content of the auxiliary functional component in the composition ranges from 0% to 20%, preferably, 0.1% to 20.0%, more preferably, 0.1% to 10.0%.

14. The photosensitive resin composition according to claim 13, wherein the auxiliary functional component comprises any one or a combination of two or more of the group consisting of: gelatin and acrylic acid-derived gelatin, hyaluronic acid and acrylic acid-derived hyaluronic acid, chitosan and modified chitosan, cellulose and carboxymethyl cellulose, alginate and modified alginate, collagen, agarose and cell nutrient solution, and/or, a block polymer of multi-armed or linear polyethylene glycol polyester whose terminal group is modified by acrylate.

15. The photosensitive resin composition according to claim 14, wherein in the block polymer of multi-armed or linear polyethylene glycol polyester, the polyester chain portion is selected from any one or a combination of two or more of the group consisting of: polylactide, polyglycollide, glycolide, lactide copolymer and polycaprolactone; and/or,
  molecular weight of the polyester chain portion ranges from 800 Da to 80000 Da; and/or,
  molecular weight of the PEG chain portion ranges from 800 Da to 80000 Da; and/or,
  in the block polymer of the multi-armed polyethylene glycol polyester, the number of arms ranges from 3 to 8.

16. The photosensitive resin composition according to claim 13, wherein the auxiliary functional component is acrylic acid-derived hyaluronic acid, acrylic acid-derived gelatin or a block polymer of multi-armed polyethylene glycol polycaprolactone whose terminal group is modified by acrylate.

17. A hydrogel obtained by 3D-printing the photosensitive resin composition according to claim 7.

* * * * *